United States Patent [19]

Trecha

[11] Patent Number: 5,031,203
[45] Date of Patent: Jul. 9, 1991

[54] COAXIAL LASER TARGETING DEVICE FOR USE WITH X-RAY EQUIPMENT AND SURGICAL DRILL EQUIPMENT DURING SURGICAL PROCEDURES

[76] Inventor: Randal R. Trecha, 3613 Bethel Rd., Columbia, Mo. 65203

[21] Appl. No.: 477,728

[22] Filed: Feb. 9, 1990

[51] Int. Cl.⁵ ............................................... A61B 6/08
[52] U.S. Cl. .................................. 378/205; 378/206; 350/600; 128/898
[58] Field of Search .............. 378/206, 207, 205; 350/600, 394; 128/898

[56] References Cited

U.S. PATENT DOCUMENTS

| | | | |
|---|---|---|---|
| 3,728,027 | 4/1973 | Watanabe | 356/13 |
| 3,854,836 | 12/1974 | Weissman | 408/14 |
| 4,002,403 | 1/1977 | Mailozzi et al. | 350/600 |
| 4,065,211 | 12/1977 | Vig | 356/152 |
| 4,078,869 | 3/1978 | Honeycutt | 408/16 |
| 4,123,660 | 10/1978 | Horwitz | 250/491 |
| 4,132,900 | 1/1979 | Smith et al. | 378/206 |
| 4,167,675 | 9/1979 | Stödberg et al. | 378/206 |
| 4,223,227 | 9/1980 | Horwitz | 250/491 |
| 4,296,329 | 10/1981 | Mirabella | 250/491 |
| 4,337,502 | 6/1982 | Lescrenier | 362/32 |
| 4,426,726 | 1/1984 | Cheetham | 378/206 |
| 4,442,533 | 4/1984 | Lescrenier | 378/21 |
| 4,625,718 | 12/1986 | Olerud et al. | 128/92 |
| 4,659,185 | 4/1987 | Aughton | 350/394 |

Primary Examiner—Edward P. Westin
Assistant Examiner—Kim-Kwok Chu
Attorney, Agent, or Firm—Basile and Hanlon

[57] ABSTRACT

In an x-ray machine having an x-ray gun portion for emitting x-ray radiation along a longitudinal axis and an x-ray collector portion spaced from the gun portion along the longitudinal axis for receiving the x-ray radiation, the present invention provides a laser light emitting member disposed on the x-ray gun portion for emitting a beam of visible laser light. A target grid member is disposed on the x-ray collector portion for targeting the visible laser light in coaxial relationship with the longitudinal axis of the x-ray radiation between the gun portion and the collector portion. One or more radiolucent laser light redirecting members are provided for adjustably redirecting the visible laser light from the laser light emitting member into coaxial alignment with the longitudinal axis of the x-ray radiation to give a visual indication of the central longitudinal axis of the x-ray radiation.

17 Claims, 3 Drawing Sheets

COAXIAL LASER TARGETING DEVICE FOR USE WITH X-RAY EQUIPMENT AND SURGICAL DRILL EQUIPMENT DURING SURGICAL PROCEDURES

FIELD OF THE INVENTION

The present invention relates to an aiming apparatus, more particularly a coaxial laser targeting device, for use with an x-ray machine and surgical drill equipment during surgical procedures.

BACKGROUND OF THE INVENTION

An aiming apparatus for making transverse bores in bones in register with bores of an osteosynthesis aid has previously been disclosed in U.S. Pat. No. 4,625,718. This apparatus includes a holder for the accommodation of an aiming member adapted to be brought into the beam path of an x-ray apparatus. The reception head of the apparatus is made of a material transparent to x-ray radiation and is rotatably supported in the holding means for the accommodation of a drill or a drill wire, and a powered driving machine is arranged at the holding means for rotatably driving the reception head. The aiming apparatus of this patent serves to detect a point where to perform the transverse bore in the bone, and at the same time serves to make a preliminary bore. As the reception head for a drill or drill wire is transparent to the x-ray radiation, the drill appears as a point on the image screen. The point is brought into register with a transverse bore of the interlocking nail in the process of aiming. This done, the drilling action is performed for the soft components and the bone with the aid of the drill or drill wire respectively. Following this, the aiming apparatus is removed and the boring action is carried out via the drill wire or drill, respectively, with the aid of a hollow drill for the suitable bore screw. Following this, the drill wire or primary drill, respectively, is removed. When using a drill wire or a suitable drill, respectively, in connection with the aiming apparatus, the diameter is relatively small so that the boring action may be performed with the aid of the hollow drill. While this device is apparently effective, it is relatively large and awkward to work with, requiring numerous x-ray exposures in order to assure accurate aligning of the drill or drill wire respectively with the bore of the osteosynthesis aid during surgery, and in addition is rather difficult to sterilize properly as is required for use in operating rooms.

An image plane indicator for visibly defining the image plane located at the movable fulcrum of a tomography x-ray machine is disclosed in U.S. Pat. No. 4,442,533. The indicator of this patent includes a laser beam light source mounted for vertical movement along a rack and pinion assembly. As the fulcrum of the x-ray machine is raised or lowered with respect to the patient to take x-ray images along different horizontal planes, a pulse generator generates a signal responsive to the movement. The signal operates a servo-drive mechanism that moves the light source a corresponding vertical distance along the rack and pinion assembly. This indicator visually defines the image plane located at the movable fulcrum of the tomography x-ray machine, and does not provide an indication of the longitudinal axis of the central x-ray beam as would be required when making transverse bores in a patient's bone in register with the bores of a osteosynthesis aid in the bone.

Laser light beams have also been used to calibrate tomography machines using phantoms as disclosed in U.S. Pat. No. 4,296,329, and for calibrating linear accelerators, or a cobalt-60 teletherapy machine as is disclosed in U.S. Pat. No. 4,123,660 and U.S. Pat. No. 4,223,227.

SUMMARY OF THE INVENTION

The present invention as hereinafter disclosed is used to locate interlocking screw holes in intramedullary rods. The present invention can also be used for placement of pedicle screws in spinal surgery; placement of wires for percutaneous and open fixation; accurate positioning of the image intensifier without exposure to radiation; and accurate percutaneous pin placement of an external fixation in pelvic fractures. The present invention has been devised to increase the efficiency of placing interlocking screws or the like. The invention decreases radiation exposure; greatly decreases operative time; provides an accurate and reliable way to locate the drill holes necessary for placement of the transverse fixation screws; uses harmless visible light radiation; is adapted to all C-arm image intensifiers currently used in operating rooms today; requires very little instruction to operate the device successfully; has no moving parts or guides; is inherently simple, requiring only one person to operate; and is extremely durable with minimal maintenance. The present invention is designed to locate the point of entry on the skin and bone for the drill point, and orientate the drill in the remaining two planes so as to place the longitudinal axis of the drill bit in line with the longitudinal axis created at the centers of the apertures in the intramedullary rod.

The present invention has two basic components. The first is a low-voltage helium neon laser of approximately 0.5 milliwatts power. These types of lasers have been cleared by the Food and Drug Administration for use in the operating room. A radiolucent plastic mirror assembly is mounted on the laser. The mirror is adjustable and will broadcast the laser beam 90° with respect to the original ray emitted by the laser. In the disclosed embodiments of the present invention, the laser can be mounted either externally or internally to the x-ray gun portion of the C-arm image intensifier. The second component is a target grid which is simply a plastic disk approximately the size of the collector plate of the C-arm image intensifier, with metal wires embedded in the disk at 90° to form a cross-hair type of arrangement.

The laser is mounted on the gun side of the C-arm image intensifier, and the target grid is centered on the collector plate. The central ray of the x-ray shares the path of the laser as it is reflected off the mirror, so that the x-ray and the laser are coaxial with one another. The target grid is mounted on the collector so as to be centered on the monitor. The laser beam is adjusted so that it will strike the target grid at the intersection of the cross-hairs.

When the surgeon is ready to place the distal screws, he will center the distal apertures on the monitor, creating a true circle centered over the cross-hairs. Next the x-ray is turned off and will not be used for the remainder of this localization. The laser is then activated. The laser light beam is now coaxial with the previous x-ray, as well as with the axis of the two apertures which were previously aligned during the x-ray procedure. The laser spot can easily be seen on the lateral side of the leg or other portion of the body of the patient. The incision is then made in the leg or other body portion where indicated by the laser spot to expose the drill site on the bone. The laser spot is then visible on the exposed bone. The point of the drill is placed directly on the laser light spot where it indicates that the drilling should begin. The drill is then pivoted about the drill point into a position, such that the laser spot strikes the back of the drill in alignment with the longitudinal axis of the drill bit. Now the x-ray, the laser and the drill bit share the same central coaxial longitudinal axis. At this point the longitudinal axis of the drill bit is defined by a line which is identical to the central axis of the x-ray and the laser beam. Drilling can now be completed. As the drill is advanced, it is kept in this orientation with the laser beam striking the back of the drill at a point in alignment with the longitudinal axis of the drill bit. Again, this portion of the procedure is performed without x-ray monitoring.

Other advantages and applications of the present invention will be come apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DETAILED DESCRIPTION OF THE PREFERRED EMBODIMENT

Figure 1:
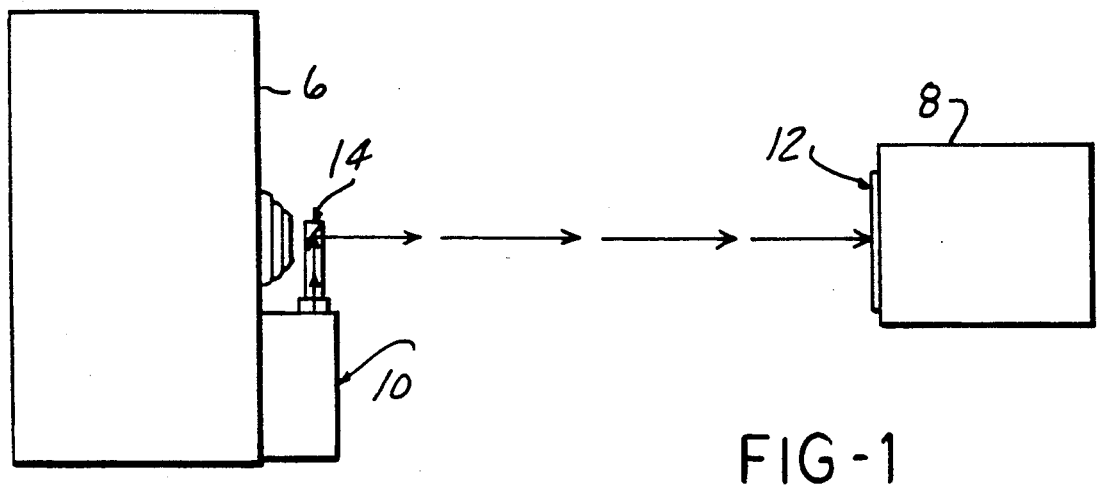
FIG. 1 is a schematic diagram showing the present invention mounted externally on an x-ray gun portion of a C-arm image intensifier in a retrofit configuration for broadcasting a laser beam coaxial with the x-ray beam toward a target grid positioned on a collector of the C-arm image intensifier.

The basic configuration of the present invention is shown schematically in FIG. 1. The present invention can be installed as a retrofit of existing x-ray equipment, wherein the existing x-ray equipment includes an x-ray gun portion 6 for emitting x-ray radiation along a longitudinal axis, and an x-ray collector portion 8 spaced from the gun portion 6 along the longitudinal axis for receiving the x-ray radiation. The present invention can also be installed on new x-ray equipment as part of the original equipment manufacturer's components installed within the x-ray gun portion 6 of the x-ray equipment as schematically shown in FIG. 5.

Figure 2:
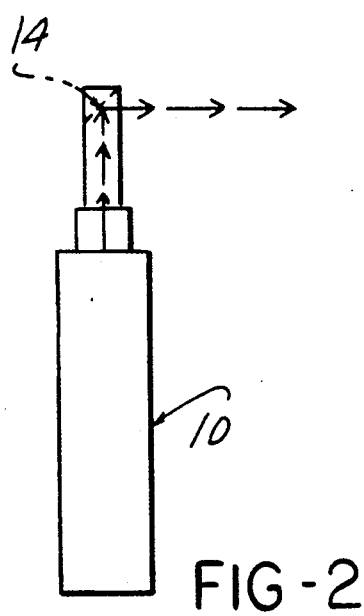
FIG. 2 is a schematic illustration of a laser emitting a beam of visible laser light and a radiolucent mirror positioned with respect to the laser.
Figure 3:
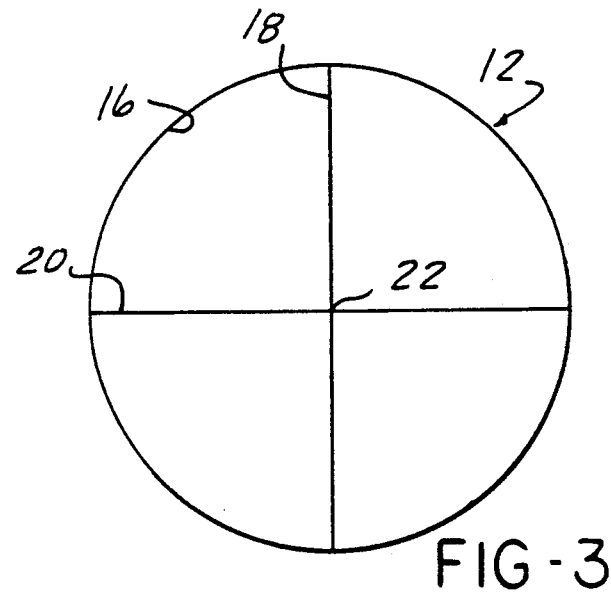
FIG. 3 is a schematic diagram of a target grid which is positioned on the collector of the C-arm image intensifier.
Figure 4:
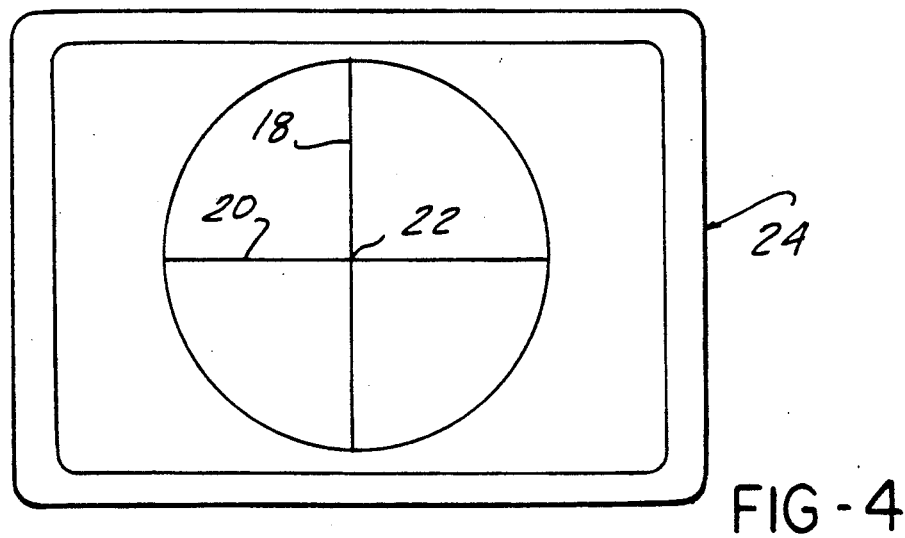
FIG. 4 is an illustration of the monitor screen for the C-arm image intensifier shown in FIG. 1.

Referring again to FIG. 1, the present invention includes laser light emitting means 10 disposed on the x-ray gun portion 6 for emitting a beam of visible laser light. Target grid means 12 are disposed on the x-ray collector portion 8 for targeting the visible laser light in coaxial relationship with the longitudinal axis of the x-ray radiation between the gun portion 6 and the collector portion 8 of the x-ray equipment. Radiolucent laser light redirecting means 14 is provided for adjustably redirecting the visible laser light from the laser light emitting means 10 into coaxial alignment with the longitudinal axis of the x-ray radiation so that the visible laser light squarely hits the center of the target grid means 12. As depicted in the retrofit system of FIG. 1, the laser light emitting means 10 can be mounted externally to the housing of the x-ray gun portion 6 of the x-ray equipment. Referring now to FIG. 2, the laser light emitting means 10 can comprise a low wattage helium neon laser of approximately 0.5 milliwatts power. These types of lasers have been cleared by the Food and Drug Administration for use in the operating room. Radiolucent laser light redirecting means 14 is mounted on the laser in this configuration. The radiolucent laser light redirecting means 14 can include a radiolucent plastic mirror assembly. The radiolucent plastic mirror assembly is adjustable and will broadcast the laser beam 90° with respect to the original beam emitted by the laser 10. Referring now to FIG. 3, the target grid means 12 can comprise a plastic disk 16 approximately the size of the collector plate of the x-ray collector portion 8 of the x-ray equipment. The plastic disk 16 has metal wires 18, 20 embedded in the disk at 90° to form a cross-hair type arrangement as shown in FIG. 2. When x-ray radiation is emitted from the x-ray gun portion 6, the x-ray radiation is received by the collector portion 8 and can be viewed on a monitor screen 24. The monitor screen 24 would provide the view illustrated in FIG. 4 after the laser light emitting means 10, target grid means 12, and radiolucent laser light redirecting means 14 are attached to the existing x-ray equipment in this retrofit configuration.

Figure 5:
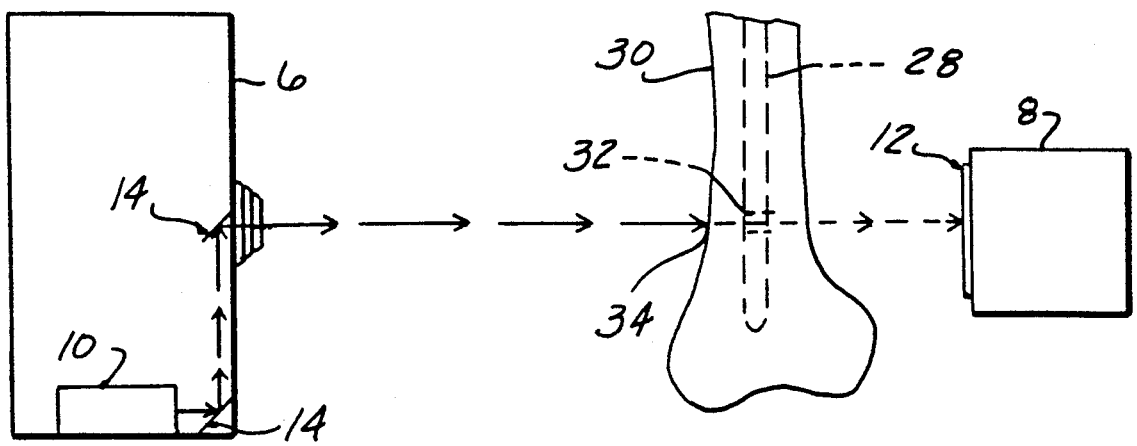
FIG. 5 is a schematic representation of an alternative mounting for the laser within the housing of the x-ray gun portion of the C-arm image intensifier as can be provided by original equipment manufacturer's with a patient's bone positioned between the x-ray gun portion and the collector portion.
Figure 10:
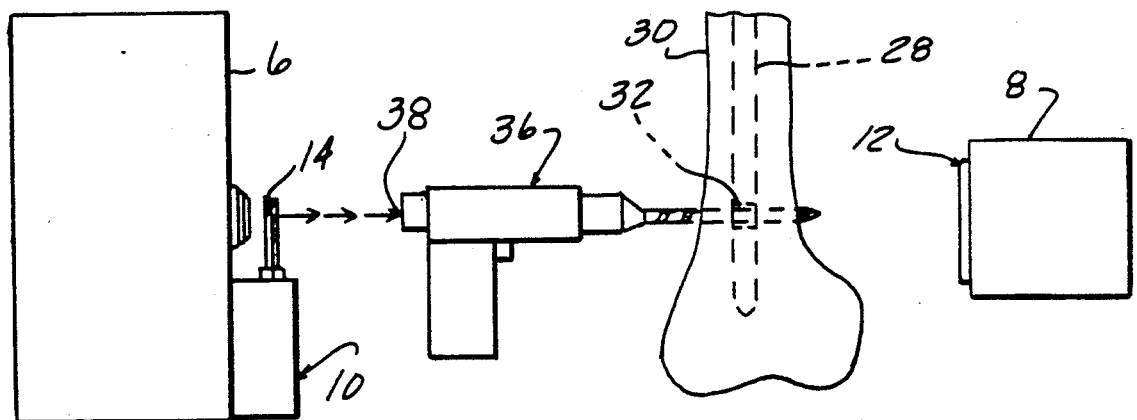
FIG. 10 is a schematic view of the drill passing through the bone and bore of the intramedullary rod.

An original equipment manufacturer's installation of the laser light emitting means 10 within the housing of the x-ray gun portion 6 of the x-ray equipment as shown in FIG. 5, would include radiolucent laser light redirecting means 14 also enclosed within the housing, and target grid means 12 disposed on the collector portion 8 of the x-ray equipment. When viewed on the monitor screen, without a portion of a patient interposed between the gun portion 6 and the collector portion 8 of the x-ray equipment, the view would be similar to that depicted in FIG. 4. In this original equipment manufacturer's configuration as shown in FIG. 5, the radiolucent light redirecting means 14 could include first and second radiolucent plastic mirror assemblies. These mirrors would be adjustable and would be capable of broadcasting the laser beam in coaxial relationship with the longitudinal axis of the x-ray radiation between the gun portion 6 and the collector portion 8 of the x-ray equipment. It should be understood from the configurations described and shown in FIGS. 1 and 5, that various mounting arrangements of the laser light emitting means 10 and radiolucent laser light redirecting means 14 are possible and are to be considered within the scope of the present invention provided that the laser light is ultimately directed in coaxial relationship with the longitudinal axis of the x-ray radiation between the gun portion 6 and the collector portion 8 of the x-ray equipment. Therefore, it is anticipated that it may require only one, or may require a plurality of radiolucent laser light redirecting means 14 in order to properly align the visible laser light beam with the longitudinal axis of the x-ray radiation depending on the mounting orientation selected for the laser light emitting means 10 with respect to the gun portion 6 of the x-ray equipment. The selection of the mounting location may in part be influenced by the space requirements for the laser light emitting means 10, and the existing space available in the original equipment manufacturer's housing for the gun portion 6 of the x-ray equipment. It should further be understood that various means for mounting the laser 10 to the housing, either internally or externally, are available, and may be selected as required as long as each component is firmly mounted in its appropriate position and orientation in a secure manner so that unintentional misalignment of the laser light beam is unlikely to occur due to vibration, movement or repositioning of the x-ray equipment.

As previously mentioned, the visible laser light beam can be used to position the C-arm image intensifier with respect to the patient. In addition, the present invention is particularly adapted for use in various surgical procedures requiring accurate drilling through a patient's bone, particularly when the aperture being drilled through the bone must be accurately aligned along a predetermined path corresponding to the longitudinal axis of the x-ray radiation beam passing between the x-ray gun portion and the collector portion of the x-ray equipment for the surgical procedure to be successful. For purposes of illustration, one such surgical procedure will be described hereinafter in detail so that the scope of the present invention can be fully appreciated. It should be understood that this surgical procedure is given for illustrative purposes only, and it is not meant to limit the scope of the present invention in any way. It should be understood that the present invention encompasses many such surgical procedures to numerous to go into detail here, and that the appropriate use and application of the invention will be apparent to those skilled in the art of surgery upon reading this disclosure.

Figure 6:
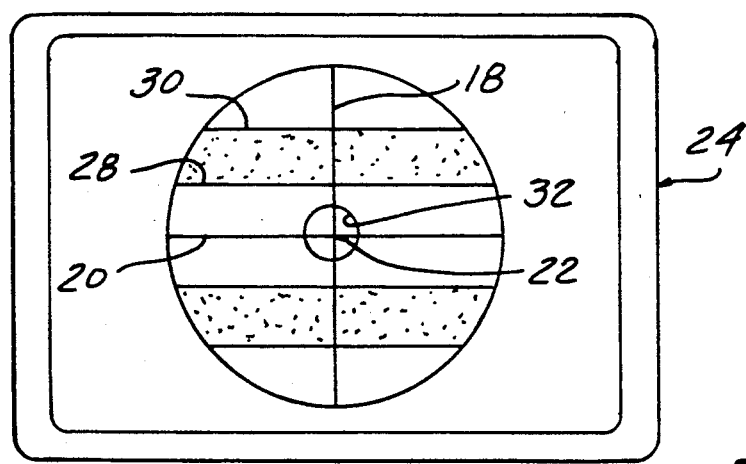
FIG. 6 is a monitor screen showing the image provided by the C-arm image intensifier as shown in FIG. 6.
Figure 7:
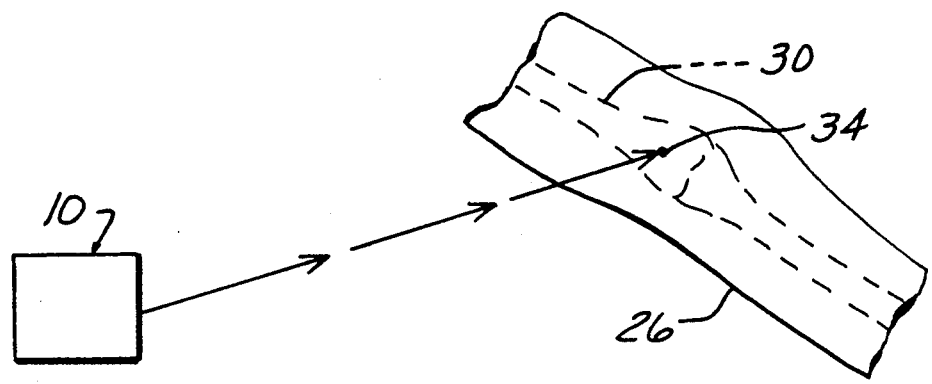
FIG. 7 is a perspective view of the laser beam forming a spot on the skin of a patient to indicate the position of an incision to be made.
Figure 8:
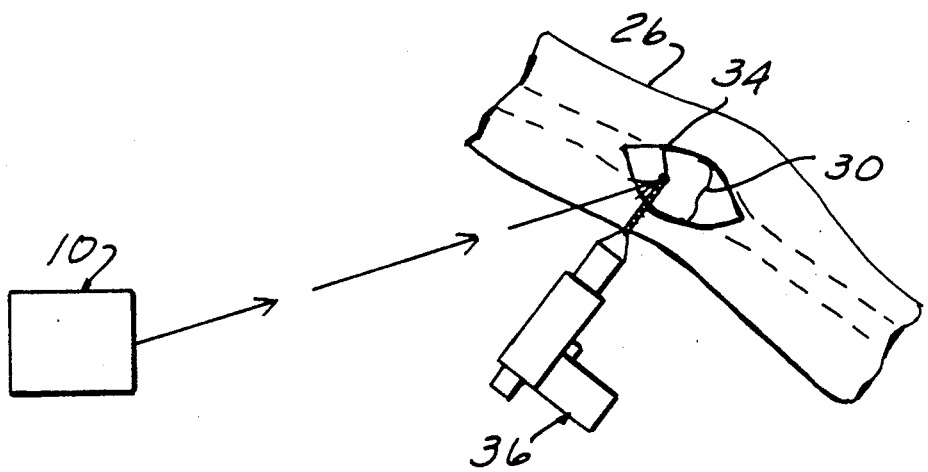
FIG. 8 is a perspective view of the laser beam forming a spot on the exposed bone after the incision has been made.
Figure 9:
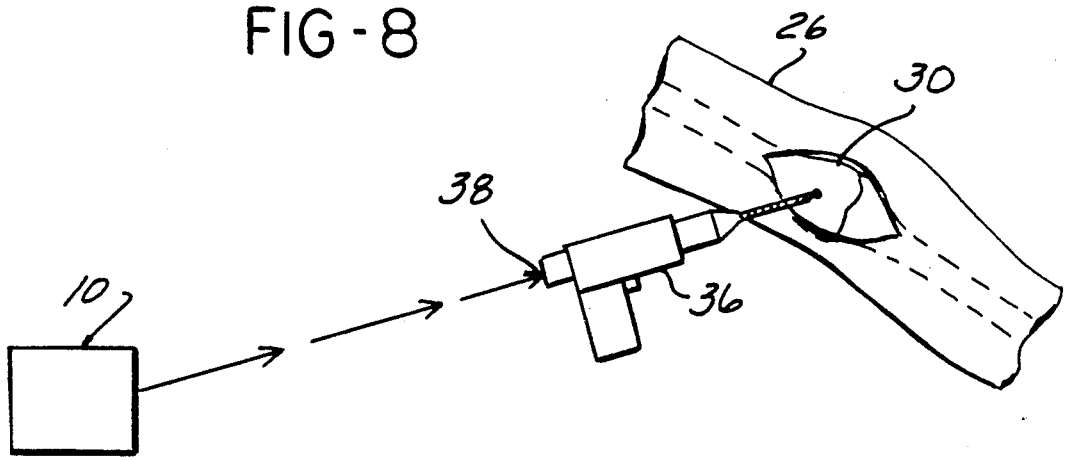
FIG. 9 is a perspective view showing the laser beam striking the back of the surgical drill in alignment with the longitudinal axis of the drill bit.

After the visible laser light beam has been adjusted so that it intersects the target grid means at its center 22 corresponding to the intersection of the cross-hairs, the patient is anaesthetized and the portion of the patient's body on which the surgical procedure is to take place is positioned between the x-ray gun portion and the collector gun portion of the x-ray equipment. For purposes of this illustration, the surgical procedure described will be that used to locate interlocking screw holes in intramedullary rods. As shown in FIG. 7, the patient's leg 26 is positioned and immobilized. The surgery having proceeded to the point where the intermedullary rod 28 is sheathingly inserted within the interior of the bone 30, it is now desired to locate the bores 32 formed in the intermedullary rod 28 that are now sheathed from view within the bone 30. Typically, a C-arm image intensifier x-ray is taken to locate the bore 32. With the present invention, when the surgeon is ready to place the distal screws, he will center the distal bore 32 on the monitor 24 creating a true circle centered over the cross-hairs as depicted in FIG. 6. The x-ray is then turned off and will not be used for remainder of this localization. The laser 10 is then activated, and since its beam has been adjusted to share the central longitudinal axis of the x-ray radiation beam, as well as the axis of the distal bore 32, a laser spot 34 can easily be seen on the lateral side of the leg 26 indicating where the incision is to be made as shown in FIG. 7 of the drawing. After the incision has been made and the bone 30 exposed, the visible laser light beam forms a laser spot 34 in the exposed bone 30 indicating where the drill point should be placed. This is depicted in FIG. 8 of the drawings. In FIG. 9 of the drawings, the drill 36 is pivoted about the drill point positioned on the exposed bone into alignment with the visible laser light beam so that the laser light beam strikes the back of the drill at a point 38 in alignment with the longitudinal axis of the drill bit. At this point, the longitudinal axis of the drill bit is defined by a line which is identical to the central longitudinal axis of the previous x-ray radiation beam and the visible light laser beam. Drilling can now be completed. As the drill 36 is advanced, it is kept in the proper orientation with the visible laser light beam striking the back of the drill at a point 38 coinciding with the longitudinal axis of the drill bit. Again, this portion of the procedure is performed without x-ray monitoring.

While the invention has been described in detail, it will be apparent to those skilled in the art that the disclosed invention may be modified. Therefore, the foregoing description is to be considered exemplary, rather than limiting, and the true scope of the invention is that defined in the following claims.

What is claimed is:

1. In an x-ray machine having an x-ray gun portion for emitting x-ray radiation along a longitudinal axis and an x-ray collector portion spaced from the x-ray gun portion along the longitudinal axis for receiving the x-ray radiation, the improvement comprising;

laser light emitting means disposed on the x-ray gun portion for emitting a single elongated beam of visible laser light;

target grid means disposed on the x-ray collector portion for targeting the single elongated beam of visible laser light in coaxial relationship with the longitudinal axis of the x-ray radiation between the x-ray gun portion and the x-ray collector portion; and radiolucent laser light redirecting means for adjustably redirecting the single elongated beam of visible laser light from the laser light emitting means into coaxial alignment with the longitudinal axis of the x-ray radiation to give a visual indication of the central longitudinal axis of the x-ray radiation between the x-ray gun portion and the x-ray collector portion of the x-ray machine.

2. The improvement of claim 1, wherein the laser light emitting means comprises a helium neon laser.

3. The improvement of claim 2, wherein the helium neon laser comprises a low wattage laser of approximately 0.5 milliwatts power.

4. The improvement of claim 1, wherein the radiolucent laser light redirecting means comprises a radiolucent plastic mirror adjustably mounted to broadcast the single elongated beam of visible laser light at 90° with respect to the original beam emitted by the laser light emitting means.

5. The improvement of claim 1, wherein the target grid means further comprises a plastic member approximately equal in size to a collector plate of the collector portion of the x-ray equipment, said plastic member adapted to be mounted on the collector plate and having metal wires embedded in the plastic member at 90° with respect to one another to form a cross-hair type arrangement.

6. The improvement of claim 5, wherein the plastic member comprises a disk.

7. In an x-ray machine having an x-ray gun portion for emitting x-ray radiation along a longitudinal axis and an x-ray collector portion spaced from the x-ray gun portion along the longitudinal axis for receiving the x-ray radiation, the improvement comprising;
   a low wattage helium neon laser of approximately 0.5 milliwatts power disposed on the x-ray gun portion for emitting a beam of visible light;
   a plastic disk approximately equal in size to a collector plate of the x-ray collector portion and adapted to be mounted on the collector plate, the disk having metal wires embedded in the plastic disk at 90° with respect to one another to form a cross-hair type arrangement for targeting the visible laser light in coaxial relationship with the longitudinal axis of the x-ray radiation between the x-ray gun portion and the x-ray collector portion;
   a radiolucent plastic mirror adapted to broadcast the visible laser light at 90° with respect to an original beam emitted from the laser, the radiolucent plastic mirror adjustably mounted for redirecting the visible laser light from the laser into coaxial alignment with the longitudinal axis of the x-ray radiation to give a visual indication of the central longitudinal axis of the x-ray radiation; and
   drill means disposed between the laser light emitting means and the target grid means, said drill means having a drill bit with a longitudinal axis in coaxial alignment with the beam of visible laser light.

8. The improvement of claim 7, laser mounted externally on the gun portion of C-arm image intensifier x-ray equipment.

9. The improvement of claim 7, wherein the laser is mounted internally within the gun portion of C-arm image intensifier x-ray equipment.

10. The improvement of claim 1 further comprising:
    drill means disposed between the laser light emitting means and the target grid means, the drill means having a drill bit with a longitudinal axis in coaxial alignment with the single elongated beam of visible laser light.

11. A coaxial target laser aiming device for use with x-ray radiography equipment and drill equipment comprising:
    x-ray gun means for emitting x-ray radiation along a longitudinal axis;
    x-ray collector means spaced along the longitudinal axis from the x-ray gun means for receiving the x-ray radiation;
    laser light emitting means disposed on the x-ray gun means for emitting a single elongated beam of visible laser light;
    target grid mean disposed on the x-ray collector means for targeting the single elongated beam of visible laser light in coaxial alignment with the longitudinal axis of the x-ray radiation passing between the x-ray gun means and the x-ray collector means;
    radiolucent laser light redirecting means for adjustably redirecting the single elongated beam of visible laser light from the laser light emitting means into coaxial alignment with the longitudinal axis of the x-ray radiation passing between the x-ray gun means and the x-ray collector means; and
    drill means disposed between the laser light emitting means and the target grid means, the drill means having a drill bit with a longitudinal axis in coaxial alignment with the single elongated beam of visible laser light.

12. The device of claim 11, wherein the laser light emitting means comprises a helium neon laser.

13. The device of claim 12, wherein the helium neon laser comprises a low wattage laser of approximately 0.5 milliwatts power.

14. The device of claim 11, wherein the radiolucent laser light redirecting means comprises a radiolucent plastic mirror adjustably mounted to broadcast the single elongated beam of visible laser light at 90° with respect to the original beam emitted by the laser light emitting means.

15. The device of claim 11, wherein the target grid means further comprises a plastic member approximately equal in size to a collector plate of the x-ray collector means, said plastic member adapted to be mounted on the collector plate and having metal wires embedded in the plastic member at 90° with respect to one another to form a cross-hair type arrangement.

16. The device of claim 11, further comprising a C-arm image intensifier having an x-ray gun means portion and an x-ray collector means portion with said laser light emitting means disposed on the x-ray gun means portion of the C-arm image intensifier.

17. The device of claim 11, further comprising a C-arm image intensifier having an x-ray gun means portion and an x-ray collector means portion with said laser light emitting means mounted internally within the x-ray gun means portion of the C-arm image intensifier.

* * * * *

UNITED STATES PATENT AND TRADEMARK OFFICE
CERTIFICATE OF CORRECTION

PATENT NO. : 5,031,203

DATED : July 9, 1991

INVENTOR(S) : Randal R. Trecha

It is certified that error appears in the above-identified patent and that said Letters Patent is hereby corrected as shown below:

Column 7, line 45, before "laser mounted" insert --further comprising the low wattage helium neon--.

Column 7, line 46, before "gun portion" insert --x-ray--.

Column 7, line 48, delete "wherein the" and insert --further comprising the low wattage helium neon--.

Column 7, line 48, delete "is".

Column 7, line 49, before "gun portion" insert --x-ray--.

Signed and Sealed this

Twenty-first Day of July, 1992

Attest:

DOUGLAS B. COMER

*Attesting Officer*      *Acting Commissioner of Patents and Trademarks*